United States Patent [19]

de Kraa et al.

[11] Patent Number: 4,671,946

[45] Date of Patent: Jun. 9, 1987

[54] PROCESS AND APPARATUS FOR THE REMOVAL OF HYDROGEN SULPHIDE FORM A GAS MIXTURE

[75] Inventors: Johannes A. de Kraa; Jannes J. Zomerman, both of The Hague, Netherlands

[73] Assignee: Shell Oil Company, Houston, Tex.

[21] Appl. No.: 883,664

[22] Filed: Jul. 9, 1986

[30] Foreign Application Priority Data

Jul. 15, 1985 [NL] Netherlands ................. 8502026

[51] Int. Cl.[4] ................. C01G 1/04; C01B 17/16; C01B 31/20
[52] U.S. Cl. ................................. 423/230; 423/416
[58] Field of Search ............. 423/416, 230; 55/73

[56] References Cited

U.S. PATENT DOCUMENTS

| | | | |
|---|---|---|---|
| 2,614,066 | 10/1952 | Cornell | 423/564 |
| 4,305,733 | 12/1981 | Scholz et al. | 55/73 |
| 4,522,793 | 6/1985 | Larson et al. | 423/416 |
| 4,533,373 | 8/1985 | Butz et al. | 55/73 |

*Primary Examiner*—John Doll
*Assistant Examiner*—Lori S. Freeman
*Attorney, Agent, or Firm*—Kimbley L. Muller

[57] ABSTRACT

Process for the removal of hydrogen sulphide from a gas mixture comprising passing the gas mixture through a reactor (2) filled with catalyst for the conversion of hydrogen sulphide to carbonyl sulphide, and separating the gas mixture leaving reactor (2) in a separator (7) at a temperature below the boiling point of carbonyl suplhide in a lighter fraction and a heavier fraction in which the carbonyl sulphide is absorbed.

5 Claims, 2 Drawing Figures

PROCESS AND APPARATUS FOR THE REMOVAL OF HYDROGEN SULPHIDE FROM A GAS MIXTURE

FIELD OF INVENTION

The invention relates to a process for removing hydrogen sulphide from a gas mixture comprising hydrocarbons, hydrogen sulphide and carbon dioxide. Examples of such a gas mixture are natural gas, or a hydrocarbon-containing gas mixture given off during the production of petroleum.

In a known process for the removal of hydrogen sulphide from a gas mixture, the gas mixture is contacted with a suitable liquid absorbent that absorbs almost all the hydrogen sulphide, giving a purified gas mixture containing almost no hydrogen sulphide and a hydrogen sulphide-loaded absorbent, which absorbent is subsequently regenerated, giving a regeneration off-gas with a high hydrogen sulphide content.

It is also known to absorb hydrogen sulphide by molecular sieves. The adsorbed hydrogen sulphide is then desorbed by means of regeneration gas, giving a regeneration off-gas with a high hydrogen sulphide content.

In both cases, the regeneration off-gas is fed to a hydrogen sulphide processing installation, such as a Claus unit.

The known processes are, however, too expensive for the removal of hydrogen sulphide from a gas mixture with a very low hydrogen sulphide content.

BACKGROUND OF THE INVENTION

In a presentation "Advances in molecular sieve technology for natural gas sweetening" by Turnock and Gustafson, presented at the 22nd Annual Gas Conditioning Conference, the University of Oklahoma, April, 1972, conversion of $H_2S$ into COS has been disclosed, however, such a conversion is considered to be disadvantageous, and concentrating $H_2S$ in the heavier hydrocarbon fraction has not been disclosed.

OBJECTS AND EMBODIMENTS

The object of the invention is to provide a cheap process for the removal of hydrogen sulphide from a gas mixture.

The process for the removal of hydrogen sulphide from a gas mixture containing hydrocarbons, hydrogen sulphide and carbon dioxide thereto comprises:

(a) passing the gas mixture through a reactor which is filled at least partly with a catalyst suitable for the conversion of hydrogen sulphide to carbonyl sulphide;

(b) passing the gas mixture leaving the reactor to a separator where, at a temperature below the boiling point of carbonyl sulphide at the pressure prevailing in the separator, a lighter hydrocarbon fraction is separated from a heavier hydrocarbon fraction in which the carbonyl sulphide is absorbed; and (c) discharging from the separator separately from each other the heavier hydrocarbon fraction containing the carbonyl sulphide.

The invention further relates to an apparatus for the removal of hydrogen sulphide from a gas mixture comprising hydrocarbons, hydrogen sulphide and carbon dioxide, which apparatus comprises a reactor which is filled at least partly with a catalyst suitable for the conversion of hydrogen sulphide to carbonyl sulphide and provided with a supply line and a discharge line, and a separator connected to the discharge line and provided with an upper discharge line and a lower discharge line.

DETAILED DESCRIPTION OF THE INVENTION

Figure 1:
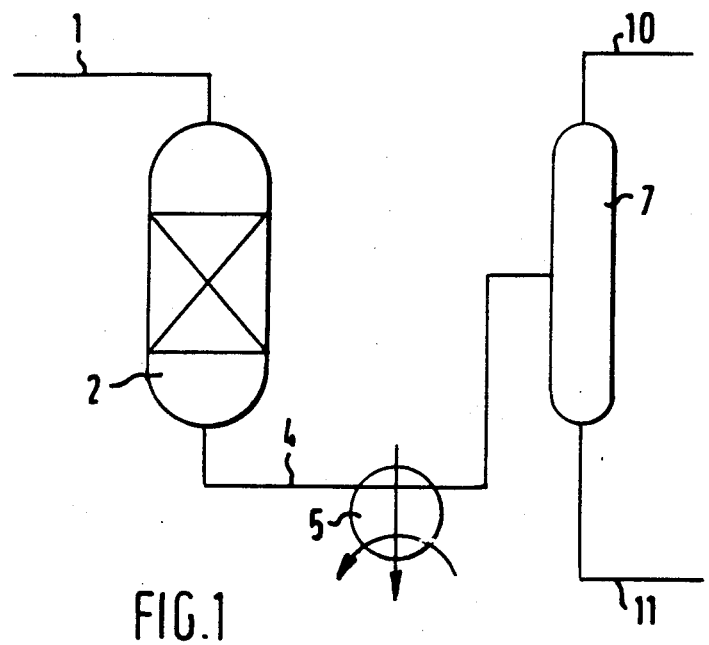
Figure 2:
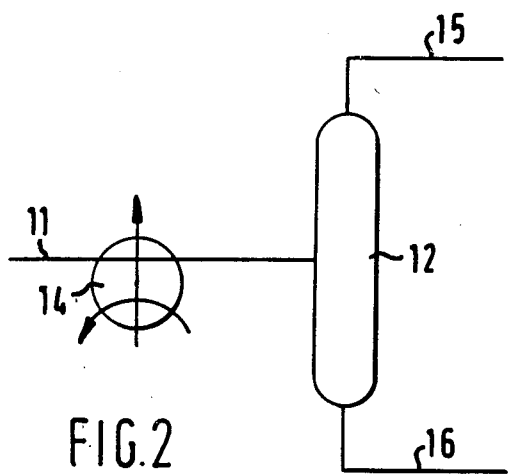

The invention will now be discussed in greater detail with reference to the drawings, in which:

FIG. 1 shows schematically a simple arrangement for the removal of hydrogen sulphide from a gas mixture; and FIG. 2 shows schematically an additional separator which can be connected to the arrangement shown in FIG. 1.

The arrangement according to FIG. 1 comprises a supply line 1 connected to a reactor 2 which is filled at least partly with a catalyst suitable for the conversion of hydrogen sulphide to carbonyl sulphide, a discharge line 4 connected to the reactor 2, a heat exchanger 5 fitted in the discharge line 4, and a separator 7 into which the discharge line 4 discharges, which separator 7 is provided with an upper discharge line 10 and a lower discharge line 11.

During operation of the apparatus, a gas mixture comprising hydrocarbons and hydrogen sulphide is fed to the reactor 2 via the supply line 1. The composition of the gas will generally be 50-95% vol. methane, 2-20% vol. ethane, 0.3-20% vol. propane, 0.4-15% vol. nitrogen, 0.5-3% vol. carbon dioxide, 1-100 ppm (volume parts per million volume parts) hydrogen sulphide, and the rest comprising heavier hydrocarbon fractions, such as butane, pentane, hexane, etc.

In the reactor 2 at least a part of the hydrogen sulphide is converted into carbonyl sulphide according to the reaction $H_2S + CO_2 \rightarrow COS + H_2O$. This reaction is catalyzed by the catalyst present in the reactor 2.

The gas mixture leaving the reactor 2 then passes through the discharge line 4 to the heat exchanger 5 where the gas mixture is brought to a temperature above the boiling point of ethane at the pressure prevailing in the separator 7 and below the boiling point of carbonyl sulphide at that pressure. At this temperature the mixture is passed to the separator, from which the gaseous lighter hydrocarbon fraction, methane and ethane, is discharged via the upper discharge line 10, and from which the liquid heavier hydrocarbon fraction, comprising propane, butane, pentane, hexane, etc. together with the carbonyl sulphide, is discharged via the lower discharge line 11.

The liquid is led through the lower discharge line 11 to a unit for the removal of carbonyl sulphide. As such an apparatus is known per se, it will not be shown and the process for the removal of carbonyl sulphide will not be described.

In general, the gas fed to the reactor 2 will be at a temperature of between $-5°$ C. and $+20°$ C. and a pressure of between 5 MPa and 15 MPa. The quantity of gas will be between 0.5 and $15 \times 10^6$ Nm$^3$/day (1 Nm$^3$ gas corresponds to a m$^3$ gas at a temperature of 0° C. and a pressure of 0.1 Mpa). The temperature of the gas mixture in the separator will be between $-80°$ C. and $+20°$ C. The gas speed in the reactor 2 will not exceed 0.3 m$^3$/s per m$^2$ surface area of the reactor 2 in an unfilled state.

The catalyst in the reactor 2 should be suitable to catalyze the conversion of hydrogen sulphide to carbonyl sulphide. Suitable catalysts for this purpose are, for example, molecular sieves such as zeolites and alkali or alkaline earth aluminum silicates with pore diameters of between $3\times10^{-10}$ m and $10\times10^{-10}$ m. Molecular sieves are, moreover, able to absorb water, so that the equilibrium in the above-mentioned reaction is shifted towards the carbonyl sulphide side.

If the lighter hydrocarbon fraction which leaves the separator 7 via the upper discharge line 10 is only to contain methane, the gas mixture must be cooled in the heat exchanger 5 to a temperature above the boiling point of methane at the pressure prevailing in the separator and lower than the boiling point of ethane at that pressure. The mixture discharged via the lower discharge line 11 will in that case additionally contain ethane. In order to separate ethane from this mixture, the mixture is passed through the bottom discharge line 11 to an additional separator 12 (see FIG. 2) via a heat exchanger 14, where it is brought to a temperature above the boiling point of ethane at the pressure prevailing in the additional separator 12 and below the boiling point of carbonyl sulphide at that pressure, which temperature is higher than that in the separator 7. This temperature will in general lie between 40° C. and 80° C. It is also possible to lower the pressure of the gas before it is fed into the additional separator 12. Ethane is removed from the additional separator 12 via an upper discharge line 15, and the heavier hydrocarbon fraction with carbonyl sulphide is discharged via a lower discharge line 16. As has been discussed for FIG. 1, the carbonyl sulphide can be removed from the heavier hydrocarbon fraction by a known method.

Instead of directly separating carbonyl sulphide from the mixture of heavier hydrocarbon fraction and carbonyl sulphide, the carbonyl sulphide can first be separated from the mixture together with propane.

To this end, the mixture is led to a second additional separator (not shown) via a heat exchanger in which the mixture is brought to a temperature below the boiling point of butane at the pressure prevailing in the second additional separator and above the boiling point of carbonyl sulphide at that pressure. The gas mixture leaving the top of the second additional separator will then contain propane and carbonyl sulphide, and the mixture leaving the bottom will contain the heavier hydrocarbon fraction comprising butane, pentane, hexane, etc. In this case as well, the pressure of the gas mixture can, if desired, be lowered before it is fed into the second additional separator. If the temperature of the gas mixture led to the second additional separator is below the boiling point of pentane and above the boiling point of propane, the gas mixture leaving the top of the second additional separator will contain propane, butane and carbonyl sulphide, while the gas mixture leaving the bottom of this separator will contain the heavier hydrocarbon fraction.

The second additional separator can either be connected to the lowe discharge line 11 (see FIG. 1) or to the lower discharge line 16 (see FIG. 2).

If the quantity of the heavier hydrocarbon fraction in the gas mixture that is fed through the line 1 (see FIG. 1) to the reactor 2 is too small to separate all the carbonyl sulphide formed in the reactor 2 from the lighter hydrocarbon fraction, or if the gas mixture only contains hydrogen in the form of methane and ethane, then a material having a boiling point greater than ethane, such as propane, can be added to the gas mixture before it is cooled in the heat exchanger 5.

This propane can be added to the gas mixture before it is fed into the reactor 2 or after it leaves the reactor 2 and before it is cooled. The gas mixture is cooled to such a temperature that the gaseous lighter hydrocarbon fractions can be removed from the separator 7 via the upper discharge line 10 and the propane with the carbonyl sulphide in liquid form via the lower discharge line 11.

The carbonyl sulphide can be removed from propane in a known manner, after which the propane can again be added to the gas mixture as described above.

Instead of the propane, any other material can be used with a higher boiling point than ethane, for example butane or pentane.

Since the heavier hydrocarbon fraction has a volume that is less than about 20% of the total volume of the gas supplied per unit time, the carbonyl sulphide formed from the hydrogen sulphide will, in the process according to the invention, be absorbed in this smaller volume. This means that it is sufficient to use an apparatus for the removal of hydrogen sulphide from the total volume of gas. The invention is therefore attractive because the production of relatively small amounts of gaseous hydrocarbons contaminated with hydrogen sulphide now becomes economically feasible.

What we claim as our invention is:

1. A process for the removal of hydrogen sulphide from a gas mixture containing said hydrogen sulphide, hydrocarbons and carbon dioxide which comprises:
    (a) passing said gas mixture through a reactor containing at least in part a catalyst suitable for the conversion of said hydrogen sulphide to carbonyl sulphide and to provide a reactor effluent containing said carbonyl sulphide;
    (b) adding to said reactor effluent a material having a boiling point greater than ethane at the pressure prevailing in the hereinafter described separation zone of step (c);
    (c) passing said reactor effluent with said added material with increased content of said carbonyl sulphide to a separation zone at a temperature below the boiling point of carbonyl sulphide at the pressure prevailing in said separation zone, wherein a lighter hydrocarbon fraction is separated from a heavier fraction boiling above carbonyl sulphide and where said carbonyl sulphide is absorbed in said heavier fraction boiling above carbonyl sulphide; and
    (d) discharging from said separation zone two separate streams comprising a first hydrocarbon stream substantially free of said hydrogen sulphide and said carbonyl sulphide and said heavier fraction boiling above said carbonyl sulphide having said carbonyl sulphide dissolved therein.

2. A process for the separation of hydrogen sulphide from a hydrocarbon fraction containing hydrogen sulphide, carbon dioxide and hydrocarbons including ethane, methane and hydrocarbons boiling above ethane, which process comprises:
    (a) passing said hydrocarbon fraction through a reaction zone comprising a catalyst sufficient to convert said hydrogen sulphide to carbonyl sulphide and to produce a reactor effluent stream;
    (b) adding to said reactor effluent a material having a boiling point greater than ethane at the pressure prevailing in the hereinafter described separation zone of step (d);
    (c) passing said reactor effluent stream with said added material to a heat exchange zone to change the temperature of said stream to a temperature above the boiling point of ethane at the pressure prevailing in a hereinafter specified first separation zone; and (d) passing said reactor effluent stream with said added material with temperature modification to a first separation zone wherein ethane and methane are separated from a stream comprising heavier hydrocarbons in which carbonyl sulphide is absorbed therein and which is removed from said first separation zone.

3. The process of claim 2 wherein said stream comprising heavier hydrocarbons is passed to a second separation zone at a temperature below the boiling point of said carbonyl sulphide at the pressure prevailing in said second separation, and wherein a stream containing said carbonyl sulphide is removed from said second separation zone and wherein a stream containing heavier hydrocarbons is removed from said second separation zone.

4. The process of claim 2 wherein said hydrocarbon fraction is passed through said reactor zone comprises 50-95% methane, 2-20% ethane, 0.3-20% propane, 0.4-15% nitrogen, 0.5-3% carbon dioxide and 1-100 ppm hydrogen sulphide, all calculated on volume percent.

5. The process of claim 2 wherein said catalyst sufficient to convert said hydrogen sulphide to said carbonyl sulphide is selected from the group consisting of alkali aluminum silicates and alkaline earth silicates.

* * * * *